United States Patent [19]

Kristiansen et al.

[11] 4,291,043
[45] Sep. 22, 1981

[54] 1-N,N-DIMETHYLCARBAMOYL-3(5)-ALKYL-5(3)-ALKYLTHIOALKYLTHIO-1,2,4-TRIAZOLES, A PROCESS FOR THEIR MANUFACTURE, COMPOSITIONS WHICH CONTAIN THEM AND THEIR USE IN PEST CONTROL

[75] Inventors: Odd Kristiansen, Mölin; Jozef Drabek, Oberwil, both of Switzerland

[73] Assignee: Ciba-Geigy Corporation, Ardsley, N.Y.

[21] Appl. No.: 70,215

[22] Filed: Aug. 27, 1979

[30] Foreign Application Priority Data

Sep. 6, 1978 [CH] Switzerland ............... 9374/78
Apr. 11, 1979 [CH] Switzerland ............... 3481/79
Aug. 9, 1979 [CH] Switzerland ............... 7310/79

[51] Int. Cl.³ ............... A01N 47/38; C07D 249/12
[52] U.S. Cl. ............... 424/269; 548/265
[58] Field of Search ............... 548/263, 265; 424/269

[56] References Cited

U.S. PATENT DOCUMENTS 4,054,664 10/1977 Watkins et al. ............... 548/263
4,082,765 4/1978 Kirkpatrick ............... 260/308 C
4,160,839 7/1979 Kirkpatrick ............... 424/269

FOREIGN PATENT DOCUMENTS 2412564 10/1974 Fed. Rep. of Germany ...... 548/265

*Primary Examiner*—Alton D. Rollins
*Attorney, Agent, or Firm*—Frederick H. Rabin

[57] ABSTRACT

Compounds of the formula IA and IB

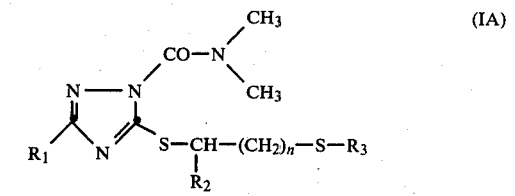

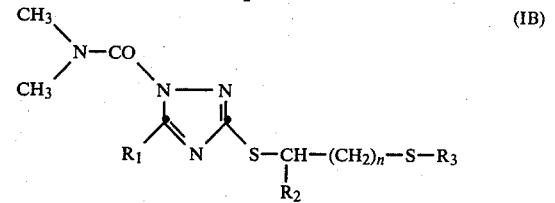

wherein $R_1$ is i-propyl, s-butyl, t-butyl or optionally methyl-substituted cyclopropyl, $R_2$ is hydrogen or methyl, $R_3$ is $C_1$–$C_4$-alkyl and n is zero or the integer 1 posess valuable pesticidal, in particular insecticidal properties.

13 Claims, No Drawings

1-N,N-DIMETHYLCARBAMOYL-3(5)-ALKYL-5(3)-ALKYLTHIOALKYLTHIO-1,2,4-TRIAZOLES, A PROCESS FOR THEIR MANUFACTURE, COMPOSITIONS WHICH CONTAIN THEM AND THEIR USE IN PEST CONTROL

The present invention relates to novel 1-N,N-dimethylcarbamoyl-3(5)-alkyl-5(3)-alkylthioalkylthio-1,2,4-triazoles which are effective against pests, a process for their manufacture, pesticidal compositions which contain these novel compounds as active component, and a method of controlling pests which comprises the use of the above triazoles.

1-N,N-Dialkylcarbamoyl-3(5)-alkyl-5(3)-hydrocarbylthio-1,2,4-triazoles which possess pesticidal, in particular insecticidal, action are known (cf. for example U.S. Pat. No. 3,308,131 and 4,066,774 and British Pat. No. 1,510,636). The present invention provides novel compounds of this type which possess a particularly good action against insects and which are especially suitable for practical use on account of their advantageous biological properties.

The novel 1-N,N-dimethylcarbamoyl-3(5)-alkyl-5(3)-alkylthioalkylthio-1,2,4-triazoles of the present invention have the formulae IA and IB

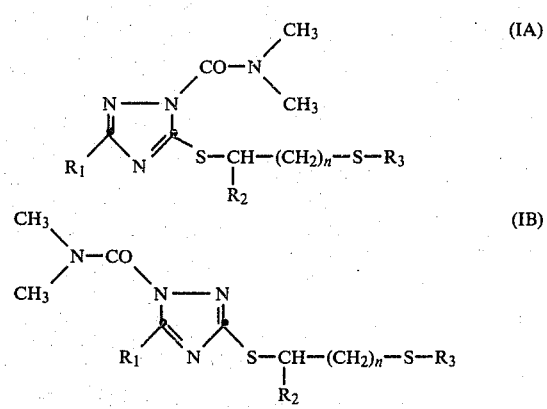

wherein $R_1$ is an i-propyl, s-butyl or t-butyl group or an optionally methyl-substituted cyclopropyl group, $R_2$ is a hydrogen atom or a methyl group, $R_3$ is a $C_1$–$C_4$ alkyl group and n is zero or 1.

Possible alkyl groups for $R_3$ are the methyl, ethyl, n-propyl and i-propyl group and the n-, i-, s- and t-butyl group.

The following substituents and combinations thereof are preferred in the compounds of the formulae IA and IB:

for $R_1$: propyl, t-butyl, cyclopropyl, 1-methylcyclopropyl and 2-methylcyclopropyl, in particular t-butyl;
for $R_2$: methyl and ethyl, in particular methyl.

The compounds of the invention can exist in the form of isomers of the above formulae IA and IB. The process for the manufacture of the compounds described herein results in mixtures of these two isomers being obtained, and in certain cases (e.g. when $R_1$ is t-butyl or 1- or 2-methylcyclopropyl and, in particular, when $R_2$ is hydrogen) the bulk of the mixture, or almost the entire product, consists of the 3-alkyl-5-alkylthioalkylthio isomer of the formula IA. Such mixtures of isomers can be separated by known methods (e.g. by chromatographic separation) into the individual isomers. However, the two isomers of the formulae IA and IB are conveniently employed in the form of their unseparated mixtures obtained by the process described herein. Accordingly, the invention is to be construed as comprising both the individual isomers of the formulae IA and IB and mixtures thereof.

The compounds of the formulae IA and IB are distinguished by their excellent insecticidal activity. In particular, they possess both a very good systemic and contact action against sucking insects, e.g. of the order Homoptera and especially of the family Aphididae (e.g. *Aphis fabae, Aphis craccivora* and *Myzus persicae*).

The compounds of the present invention also possess a particularly pronounced activity against insects of the order Coleoptera. Thus, for example, it has been found that, compared with the known insecticidal 1-N,N-dimethylaminocarbamoyl-3-tert-butyl-5-methylthio-1,2,4-triazole (cf. U.S. Pat. No. 1,066,774), the compounds of the formulae IA and IB have a markedly superior action against insect pests of the species Leptinotarsa decemlineata and Anthonomus grandis. In this connection, particular attention is also drawn to the advantageous action of the compounds of the invention against soil insects, especially against soil insects of the last mentioned order (Coleoptera).

Accordingly, the compounds of formulae IA and IB are particularly suitable for controlling plant-destructive insects in crops of cultivated plants and ornamentals, especially in crops of cotton, fruit and vegetables.

Furthermore, the compounds of the invention are also effective against plant-destructive acarids (mites), e.g. of the families Tetranychidae and Tyroglyphidae.

The compounds of formulae IA and IB are obtained by methods analogous to known ones, e.g. by reacting a compound of formula II

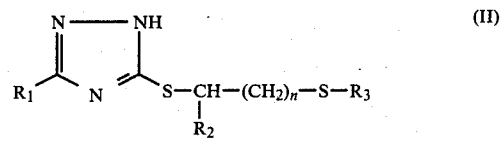

wherein $R_1$, $R_2$, $R_3$ and n are as defined for formulae IA and IB, in the presence of a base, with a N,N-dimethylcarbamoyl halide, in particular N,N-dimethylcarbamoyl chloride.

The process is advantageously carried out at a temperature between 30° and 150° C., ordinarily between 40° and 80° C., under normal or slightly elevated pressure and preferably in the presence of a solvent or diluent which is inert to the reactants.

Suitable solvents or diluents for the above process are e.g. ketones such as acetone, methyl ethyl ketone and cyclohexanone, as well as acetonitrile.

Suitable bases for the above process are in particular tertiary amines, such as trialkylamines, pyridines and dialkyl anilines; hydroxides, oxides, carbonates and bicarbonates of alkali metals and alkaline earth metals; and alkali metal alcoholates, for example potassium tert-butylate and sodium methylate.

The starting materials of formula II are new and likewise fall within the scope of the invention. They can be obtained from known precursors by methods analogous to known ones, e.g. by reacting a compound of formula III

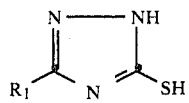

in the presence of a base (e.g. NaOC$_2$H$_5$), with a compound of formula IV

Hal—CH(R$_2$)—(CH$_2$)$_n$—S—R$_3$ (IV)

wherein R$_1$ to R$_3$ and n in the above formulae (III) and (IV) are as defined for formula I and Hal is a halogen atom.

The process for obtaining the starting material is advantageously carried out at a temperature between 60° and 100° C. and preferably in the presence of a solvent or diluent which is inert to the reactants, e.g. ethanol.

The compounds of formulae IA and IB and their mixtures are used as pure active substance or they form a constituent of compositions which additionally contain suitable carriers or adjuvants or mixtures thereof.

Suitable carriers and adjuvants can be solid or liquid and correspond to the substances conventionally used in the art of formulations, e.g. natural or regenerated substances, solvents, dispersing agents, wetting agents, tackifiers, thickeners, binders and/or fertilisers.

The insecticidal and/or acaricidal action of the compositions of the invention can be substantially broadened by addition of other acaricides and/or insecticides. Examples of suitable additives are: organophosphorus compounds, nitrophenols and derivatives thereof, formamidines, ureas, pyrethroids, carbamates, and chlorinated hydrocarbons.

The compositions of the invention can be formulated e.g. as dusts, dispersions, solutions and suspensions, and also as water-dispersible wettable powders, pastes, emulsions and emulsifiable concentrates.

Preferably, however, the above compositions are formulated as granules (e.g coated granules, impregnated granules and homogeneous granules), which are suitable for scattering onto the surface of the soil.

The content of active substance in the above compositions is between 0.1 and 95%, though higher concentrations can also be used if the compositions are applied from an aircraft or other appropriate device.

The active substances of the formula I can be formulated e.g. as follows (throughout this specification, the parts are by weight):

Granules: The following substances are used to formulate 5% granules:
5 parts of active substance,
0.25 parts of epichlorohydrin,
0.25 parts of cetyl polyglycol ether,
3.50 parts of polyethylene glycol,
91 parts of kaoline (particle size 0.3–0.8 mm).

The active substance is mixed with epichlorhydrin and the mixture is dissolved in 6 parts of acetone; the polyethylene glycol and cetyl polyglycol ether are then added. The resultant solution is sprayed on kaolin, and the acetone is subsequently evaporated in vacuo.

Emulsifiable concentrate I 20 parts of active substance are dissolved in 70 parts of xylene, and to this solution are added 10 parts of an emulsifying agent consisting of a mixture of an arylphenylpolyglycol ether and the calcium salt of dodecylbenzenesulfonic acid. The resultant emulsifiable concentrate can be diluted with water in any ratio to form a milky emulsion.

Emulsifiable concentrate II

With stirring, 5 to at most 30 parts of active substance are dissolved at room temperature in 30 parts of dibutyl phthalate, 10 parts of Solvent 200 (low viscosity, highly aromatic petroleum distillate) and 15 to 35 parts of Dutrex 238 FC (viscous highly aromatic petroleum distillate). To this solution are added 10 parts of an emulsifier mixture consisting of castor oil polyglycol ether and the calcium salt of dedecylbenzenesulfonate. The resultant emulsifiable concentrate forms milky emulsions in water.

Wettable powder

The following ingredients are intensively mixed in a mixing apparatus: 5 to 30 parts of active substance, 5 parts of an absorbent carrier (silica gel K 320 or Wessalon S), 55 to 80 parts by weight of a carrier (Bolus alba or kaolin B 24) and a dispersing agent mixture consisting of 5 parts of a sodium laurylsulfonate and 5 parts of an alkylaryl polyglycol ether. This mixture is ground to a granular size of 5–15 μm in a disc attrition mill or air jet mill. The resultant wettable powder forms a good suspension in water.

Dust 5 parts of finely ground active substance are intensively mixed with 2 parts of precipitated silicic acid and 93 parts of talcum.

The invention is illustrated in more detail by the following Examples.

EXAMPLE 1

Manufacture of 1-N,N-dimethylcarbamoyl-3-tert-butyl-5-(2-methylthioethylthio)-1,2,4-triazole (a) Manufacture of the starting material:

15 g of 2-chloroethyl-methylsulfide are added dropwise to a solution of 15.7 g of 3-tert-butyl-5-mercapto-1,2,4-triazole in ethanolic sodium ethylate (2.3 g of sodium in 300 ml of ethanol). The reaction mixture is stirred for 2 hours at 80° C., then cooled and filtered. The solvent is removed in vacuo and the residue is taken up in 300 ml of chloroform and extracted with 100 ml of water. The solvent is removed by distillation and the crude product is washed with cold petroleum ether, yielding 3-tert-butyl-5-(2-methylthioethylthio)-1,2,4-triazole of the formula

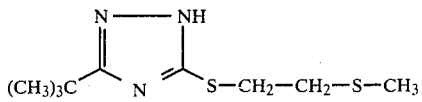

with a melting point of 114°–116° C.

The following compounds of the formula II can be obtained in analogous manner:

| R$_1$ | R$_2$ | n | R$_3$ | Physical data |
|---|---|---|---|---|
| i-C$_3$H$_7$ | H | 0 | CH$_3$ | m.p. : 122–124° C. |
| i-C$_3$H$_7$ | H | 1 | CH$_3$ | m.p. : 95–97° C. |
| i-C$_3$H$_7$ | CH$_3$ | 0 | CH$_3$ | |
| i-C$_3$H$_7$ | CH$_3$ | 1 | CH$_3$ | |

-continued

| R₁ | R₂ | n | R₃ | Physical data |
|---|---|---|---|---|
| i-C₃H₇ | H | 1 | C₂H₅ | |
| i-C₃H₇ | H | 0 | i-C₃H₇ | m.p. : 57–60° C. |
| i-C₃H₇ | H | 1 | i-C₃H₇ | m.p. : 86–90° C. |
| i-C₃H₇ | H | 0 | s-C₄H₉ | $n_D^{20} = 1.5386$ |
| t-C₄H₉ | H | 0 | CH₃ | m.p. : 122–124° C. |
| t-C₄H₉ | CH₃ | 0 | CH₃ | |
| t-C₄H₉ | CH₃ | 1 | CH₃ | m.p. : 108–112° C. |
| t-C₄H₉ | H | 1 | C₂H₅ | m.p. : 98–102° C. |
| t-C₄H₉ | CH₃ | 0 | C₂H₅ | m.p. : 139–142° C. |
| t-C₄H₉ | CH₃ | 1 | C₂H₅ | m.p. : 88–92° |
| t-C₄H₉ | H | 0 | i-C₃H₇ | |
| t-C₄H₉ | H | 1 | i-C₃H₇ | m.p. : 118–121° |
| t-C₄H₉ | H | 1 | n-C₄H₉ | |
| t-C₄H₉ | H | 1 | t-C₄H₉ | |
| s-C₄H₉ | H | 0 | CH₃ | |
| s-C₄H₉ | H | 1 | CH₃ | m.p. : 57–58° |
|  | H | 0 | CH₃ | m.p. : 80–85° |
|  | H | 1 | CH₃ | m.p. : 98–100° |
|  | CH₃ | 1 | CH₃ | |
|  | H | 1 | C₂H₅ | |
|  | H | 0 | CH₃ | m.p. : 184–186° |
|  | H | 1 | CH₃ | m.p. : 168–170° |
|  | H | 0 | CH₃ | m.p. 88–94° |
|  | H | 1 | CH₃ | m.p. 88–91° |

| Compound | R₁ | R₂ | n | R₃ | Physical data |
|---|---|---|---|---|---|
| 2 | i-C₃H₇ | H | 0 | CH₃ | $n_D^{20}$ : 1.5500 |
| 3 | i-C₃H₇ | H | 1 | CH₃ | $n_D^{20}$ : 1.5467 |
| 4 | i-C₃H₇ | CH₃ | 0 | CH₃ | |
| 5 | i-C₃H₇ | CH₃ | 1 | CH₃ | |
| 6 | i-C₃H₇ | H | 1 | C₂H₅ | $n_D^{20}$ : 1.5394 |
| 7 | i-C₃H₇ | H | 0 | i-C₃H₇ | $n_D^{20}$ : 1.5372 |
| 8 | i-C₃H₇ | H | 1 | i-C₃H₇ | $n_D^{20}$ : 1.5133 |
| 9 | i-C₃H₇ | H | 0 | s-C₄H₉ | $n_D^{20}$ : 1.5347 |
| 10 | t-C₄H₉ | H | 0 | CH₃ | m.p. : 62–64° C. |
| 11 | t-C₄H₉ | CH₃ | 0 | CH₃ | |
| 12 | t-C₄H₉ | CH₃ | 1 | CH₃ | $n_D^{20}$ : 1.5353 |
| 13 | t-C₄H₉ | H | 1 | C₂H₅ | $n_D^{20}$ : 1.5355 |
| 14 | t-C₄H₉ | CH₃ | 0 | C₂H₅ | $n_D^{20} = 1.5284$ |
| 15 | t-C₄H₉ | CH₃ | 1 | C₂H₅ | $n_D^{20}$ : 1.5301 |
| 16 | t-C₄H₉ | H | 0 | i-C₃H₇ | |
| 17 | t-C₄H₉ | H | 1 | i-C₃H₇ | $n_D^{20}$ : 1.5296 |
| 18 | t-C₄H₉ | H | 1 | n-C₄H₉ | |
| 19 | t-C₄H₉ | H | 1 | t-C₄H₉ | |
| 20 | s-C₄H₉ | H | 0 | CH₃ | $n_D^{20}$ : 1.5430 |
| 21 | s-C₄H₉ | H | 1 | CH₃ | $n_D^{20}$ : 1.5413 |
| 22 |  | H | 0 | CH₃ | $n_D^{20}$ : 1.5761 |
| 23 |  | H | 1 | CH₃ | m.p. : 39–41° C. |
| 24 |  | CH₃ | 1 | CH₃ | $n_D^{20}$ : 1.5620 |
| 25 |  | H | 1 | C₂H₅ | $n_D^{20}$ : 1.5615 |
| 26 |  | H | 0 | CH₃ | $n_D^{20}$ : 1.5654 |
| 27 |  | H | 1 | CH₃ | $n_D^{20}$ : 1.5604 |
| 28 |  | H | 0 | CH₃ | $n_D^{20}$ : 1.5660 |
| 29 |  | H | 1 | CH₃ | $n_D^{20}$ : 1.5599 |

(b) Manufacture of the end product 5.9 g of dimethylcarbamoyl chloride are added dropwise to a suspension of 11.6 g of 3-tert-butyl-5-(2-methylthioethylthio)-1,2,4-triazole and 7 g of anhydrous potassium carbonate in 200 ml of acetone. The mixture is refluxed for 4 hours, then cooled and filtered. The filtrate is concentrated and the residue is dissolved in 200 ml of chloroform and extracted with 100 ml of water. The solvent is distilled off in vacuo and the crude product is washed with petroleum ether, yielding -N,N-dimethylcarbamoyl-3-tert-butyl-5-(2-methylthioethylthio)-1,2,4-triazole of the formula

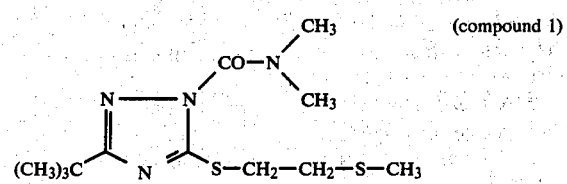

(compound 1)

in the form of white crystals with a melting point of 42°–43° C. The following compounds of the formulae IA and IB can be obtained in analogous manner:

EXAMPLE 2

Insecticidal stomach poison and contact action against *Anthonomus grandis*

Cotton plants were sprayed with an aqueous emulsion containing 0.05% of the compound to be tested (obtained from a 25% wettable powder). After the spray coating had dried, the plants were populated with adults of the species *Anthonomus grandis*. Two plants were treated with each test compound and evaluation of mortality was made 2, 4, 24 and 48 hours after the start of the test. The test was carried out at 24° C. and 26% relative humidity.

Compounds of Example 1 were effective in this test against insects of the species *Anthonomus grandis*.

EXAMPLE 3

Insecticidal stomach poison and contact action against *Leptinotarsa decemlineata*

The test method described in Example 2 was repeated using potato plants instead of cotton plants and larvae of the species *Leptinotarsa decemlineata* in the L₃-stage.

In this test, compounds of Example 1 were also effective against larvae of the species *Leptinotarsa decemlineata*.

EXAMPLE 4

Insecticidal stomach poison and contact action against *Aphis craccivora*

Pea plants (*Pisum sativum*) reared in water were each populated with about 200 insects of the species *Aphis craccivora*. The infested plants were sprayed dripping wet 72 hours later with a solution containing 200 or 100 ppm of the compound to be tested. Two plants were used for each compound and concentration and evaluation of mortality was made after a further 24 hours.

In the above test, compounds of Example 1 were very effective against insects of the species *Aphis craccivora*.

EXAMPLE 5

Insecticidal action against *Pseudococcus citri*

Bean plants (Vicia faba) which have been reared in pots and cut back to a well-developed pair of leaves, were populated with approx. 200 lice of the species *Pseudococcus citri* 24 hours before the start of the test. The undersides of the leaves populated with lice were then sprayed dripping wet next day with a test solution containing 500 ppm of the compound to be tested. Two plants were treated with each test substance and evaluation or mortality was made 24 and 48 hours respectively after the start of the test.

In this test, the compounds of Example 1 were effective against *Pseudococcus citri*.

EXAMPLE 6

Systemic insecticidal action against *Aphis craccivora*

Bean plants which had grown roots were transplanted into pots containing 600 ccm of soil and then 50 ml of a solution containing 50 ppm, 10 ppm or 1 ppm of the compound to be tested (obtained from a 25% wettable powder) were poured onto the soil.

After 24 hours the parts of the plants above the soil were populated with lice of the species *Aphis craccivora* and a plastic cylinder was then slipped over the plants to protect the lice from any possible contact with the test substance either directly or via the gas phase.

Evaluation of mortality was made 48 and 72 hours respectively after the start of the test. Two plants, each in a separate pot, were used per concentration of test substance. The test was carried out at 25° C. and 70% relative humidity.

In this test, compounds of Example 1 exhibited a good systemic action against insects of the species *Aphis craccivora*.

EXAMPLE 7

Action against plant-destructive acarids: *Tetranychus urticae* (OP-sensitive) and *Tetranychus cinnabarius* (OP-tolerant)

16 hours before the test for acaricidal action, the primary leaves of *Phaseolus vulgaris* plants were infected with an infested piece of leaf from a mass culture of *Tetranychus urticae* (OP-sensitive) or *Tetranychus cinnabarius* (OP-tolerant). (The tolerance refers to the tolerance to diazinone). The infested plants were sprayed dripping wet with a test solution containing 400 or 200 ppm of the compound to be tested. The number of living and dead imagines and larvae (all mobile stages) was evaluated under a stereoscopic microscope after 24 hours and again after 7 days. One plant was used for each test substance and test species. During the test run, the plants stood in greenhouse compartments at 25° C. In the above test, compounds of Example 1 were effective against acarids of the species *Tetranychus urticae* and *Tetranychus cinnabarius*.

What is claimed is:

1. A compound of the formula IA or IB

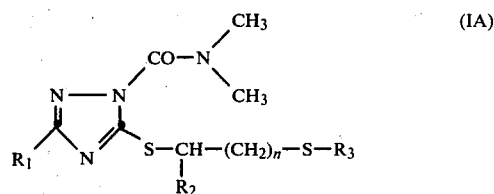

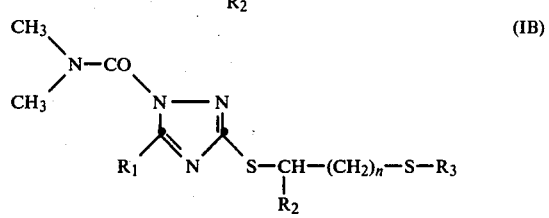

wherein $R_1$ is i-propyl, s-butyl, t-butyl or optionally methyl substituted cyclopropyl, $R_2$ is hydrogen or methyl, $R_3$ is $C_1$–$C_4$-alkyl and n is zero or the integer 1 and mixtures thereof.

2. A compound as claimed in claim 1 wherein $R_1$ is i-propyl or t-butyl, $R_2$ is hydrogen and $R_3$ is methyl or ethyl.

3. A compound as claimed in claim 2 wherein n is zero.

4. A compound as claimed in claim 1 wherein $R_1$ is i-propyl, s-butyl, t-butyl or cyclopropyl.

5. A compound as claimed in claim 4 wherein $R_1$ is t-butyl.

6. A compound as claimed in claim 4 or claim 5 wherein $R_2$ is hydrogen and $R_3$ is methyl, ethyl or n-propyl.

7. A compound as claimed in claim 1 wherein $R_1$ is t-butyl, $R_2$ is hydrogen, $R_3$ is methyl and n is the integer 1.

8. A compound as claimed in claim 1 wherein $R_1$ is t-butyl, $R_2$ is hydrogen, $R_3$ is methyl and n is zero.

9. A compound as claimed in claim 1 wherein $R_1$ is 2-methyl-cyclopropyl, $R_2$ is hydrogen, $R_3$ is methyl and n is zero.

10. A compound as claimed in claim 1 wherein $R_1$ is 1-methyl-cyclopropyl, $R_2$ is hydrogen, $R_3$ is methyl and n is the integer 1.

11. A pesticidal composition comprising a pesticidally effective amount of a compound as claimed in claim 1 together with an inert, solid or liquid diluent or carrier therefor.

12. A method of controlling insect pests at a locus, which method comprises applying to said locus a pesticidally effective amount of a compound as claimed in claim 1.

13. A method as claimed in claim 12 wherein the pests are insects which cause damage to plants.

* * * * *